(12) United States Patent
Hermanson et al.

(10) Patent No.: US 8,603,019 B1
(45) Date of Patent: Dec. 10, 2013

(54) JOINT COMPRESSION WRAP

(75) Inventors: Jon Hermanson, Knoxville, TN (US);
Jim Tipton, Kingston, TN (US); Willie York, Harriman, TN (US)

(73) Assignee: Albahealth, LLC, Rockwood, TN (US)

(*) Notice: Subject to any disclaimer, the term of this patent is extended or adjusted under 35 U.S.C. 154(b) by 238 days.

(21) Appl. No.: 13/112,534

(22) Filed: May 20, 2011

(51) Int. Cl.
*A61F 13/00* (2006.01)

(52) U.S. Cl.
USPC .............................. 602/60; 602/63

(58) Field of Classification Search
USPC ............... 602/23, 27, 60–65, 76; 2/239–241; 66/178 A, 178 R
See application file for complete search history.

(56) References Cited

U.S. PATENT DOCUMENTS

| | | |
|---|---|---|
| 1,811,786 A | 6/1931 | Frei |
| 3,975,929 A | 8/1976 | Fregeolle |
| 4,054,129 A | 10/1977 | Byars et al. |
| 4,149,274 A | 4/1979 | Garrou et al. |
| 4,150,442 A | 4/1979 | Boone |
| 4,153,050 A | 5/1979 | Bishop et al. |
| 4,153,054 A | 5/1979 | Boone |
| 4,341,095 A | 7/1982 | Poteat |
| D275,715 S | 10/1984 | Boone |
| 4,557,381 A | 12/1985 | Whitney |
| 4,745,917 A | 5/1988 | Hasty et al. |
| 5,103,656 A | 4/1992 | Hanson, II |
| 5,724,836 A | 3/1998 | Green |
| 5,814,003 A | 9/1998 | Knox et al. |
| 6,012,177 A | 1/2000 | Cortinovis |
| 6,105,173 A | 8/2000 | Brown |
| 6,216,495 B1 | 4/2001 | Couzan et al. |
| 6,371,933 B1 | 4/2002 | Gardon-Mollard |
| 6,708,348 B1 | 3/2004 | Romay |
| 7,007,517 B2 | 3/2006 | Menzies |
| 7,434,423 B1 * | 10/2008 | Reid, Jr. et al. ............ 66/178 A |
| 7,441,419 B1 * | 10/2008 | Dollyhite et al. ........... 66/178 A |
| 7,562,541 B2 | 7/2009 | Hermanson et al. |
| 7,775,069 B1 | 8/2010 | Hermanson et al. |
| 2004/0237599 A1 * | 12/2004 | Kondou et al. ................ 66/202 |
| 2009/0165190 A1 * | 7/2009 | Araki et al. ....................... 2/240 |
| 2012/0116282 A1 * | 5/2012 | Cros et al. ....................... 602/76 |

* cited by examiner

*Primary Examiner* — Michael A. Brown
(74) *Attorney, Agent, or Firm* — Dorian B. Kennedy; Baker Donelson

(57) ABSTRACT

A joint compression wrap (10) is knitted in an integrated knit format to have an oversized joint pouch (15) from which a joint crest (16) extends that is knitted in a rib stitch format that is free of wrinkles when donned. A lower limb portion (14) extends downwardly from the joint pouch and crest and has a constant compression force while an oppositely disposed upper limb portion (12) may have a graduated compression force. The upper limb portion compression force being less than the lower limb portion compression force.

15 Claims, 3 Drawing Sheets

JOINT COMPRESSION WRAP

TECHNICAL FIELD

This invention relates generally to compression wraps and more specifically to joint compression wraps for the elbow or knee that are produced in an integrated knit stitch format.

BACKGROUND OF THE INVENTION

Heretofore compression wraps have been designed to address specialized needs of both athletes and medical patients associated with pivoting joints such as the elbow or knee. Compression wraps have been used by wrapping an elongated length of stretchable material around the joint. Compression sleeves have also been developed which are stretchable, tubular devices sized to fit about the joint. The compression force of these types of devices helps minimize fatigue, keep the joints from swelling, and keep joint mechanics in the proper position. These devices, however, typically provide uniform compression along the entire length of the sleeve.

An additional problem associated with these types of sleeves and wraps is that they may provide excessive stress on the yarns and knit structures in the area of the pivoting joint while being donned, i.e., on the outside of the elbow or knee. This wrinkling can cause dermatological irritation which is commonly known as necrosis or skin shearing.

These problems have been addressed by providing a sleeve gap in the area of the elbow or knee. However this, of course, exposes the elbow or knee and stresses the gap boundary of the sleeve stitching. This approach also fails to produce a seamless product.

Accordingly, it is seen that a need remains for a joint compression wrap that can be made without seams and with different compression capabilities. It is to the provision of such therefore that the present invention is primarily directed.

SUMMARY OF THE INVENTION

In a preferred form of the invention a joint compression wrap comprises a lower limb portion configured to fit about a human limb directly below a limb joint and having a knit format and yarn to produce a first compression force, a joint crest configured to fit over the back of a human limb joint and coupled to the lower limb portion having a knit format and yarn to produce a second compression force equal to or less than the first compression force, and an upper limb portion coupled to the joint crest opposite the lower limb portion having a knit format and yarn to produce a third compression force of a graduated compression type wherein the compression force decreases along the upper limb portion from a first end adjacent the joint crest to a second end distal the joint crest.

BRIEF DESCRIPTION OF THE DRAWING

DETAILED DESCRIPTION with reference next to the drawing the seamless joint compression wrap 10 in the form of an elbow compression wrap. In FIGS. 1 and 2, the compression wrap 10 is seen to have an upper limb or arm portion 12 joined to a lower limb or arm portion 14 by a back of the elbow or posterior joint pouch 15 and a front of the elbow or anterior elbow crest 16. The top of the upper arm portion 12 is formed with an upper cuff 19. The bottom of the lower arm portion 14 is formed with a lower cuff 20. The elbow compression wrap may, of course, be produced in any number of overall sizes to fit patients of different sizes.

Figure 1:
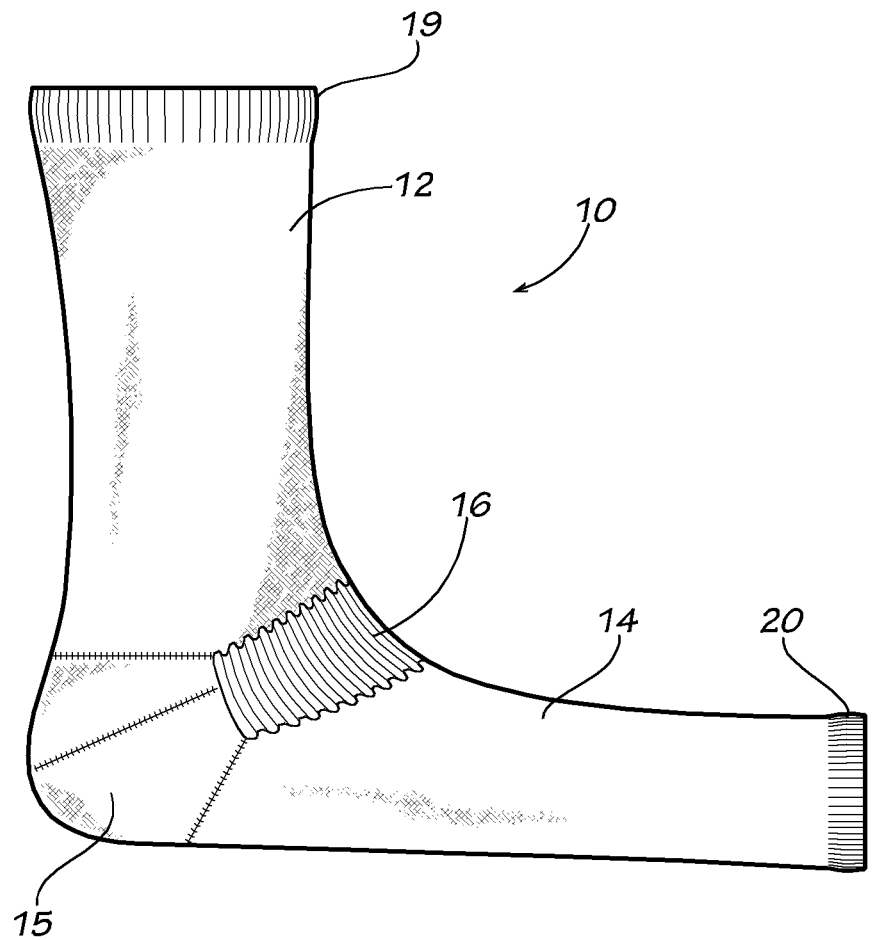
FIG. 1 is a side view of a preferred form of the joint compression wrap shown in a worn state.
Figure 2:
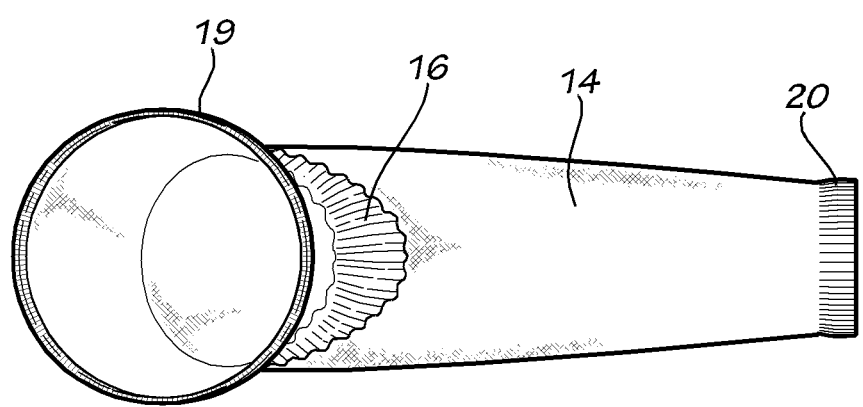
FIG. 2 is a top view of the joint compression wrap of FIG. 1.

The compression wrap is efficiently produced in an integrated knit stitch format with a knitting machine that has needle by needle selection capability in order to produce a compression wrap without seams. Exemplary of such commercial knitting machines are the Lonati Models 304 and 404. Such a machine can change the stitching needle by needle as the compression wrap is knitted in tubular form from one end to another. The machine thus can be programmed to alter the stitch format from one portion of the compression wrap to another with yarns extending continuously from one compression wrap end to the other. Thus the compression wrap can be made seamless.

With continued reference to the drawing, the upper arm portion 12 is conventionally knitted in a graduated compression format so that it is tightest when donned at its lower end adjacent the elbow pouch 15 and elbow crest 16 and gradually becomes less tight higher up the arm. This serves to force blood towards the cardiac cavity of the patient. The lower arm portion 14 is of a conventional compression knit construction, but is of a constant compression force format along the entire length of the lower arm portion rather than of a graduated compression force format. The compression force of the upper arm portion is preferably 40% to 50% of the compression force of the lower arm portion to prevent a tourniquet effect upon the veins, thereby pinching the veins, which would cause blood to pool within a wearer's lower arm. The compression force of the upper arm portion should not exceed 75% of the compression force of the lower arm portion. Additionally, the compression force of the upper arm portion is preferably 50% of the compression force of the elbow crest 16, while the compression force of the lower arm portion is approximately that of the elbow crest 16. Typically, the elbow crest 16 has a compression force of between 18 and 20 mm of mercury and the upper arm portion has an end which commences adjacent the elbow crest 16 with a compression force of approximately 18 mm of mercury and terminates at an opposite end adjacent the cuff, or distal the elbow crest 16, with a compression force of approximately 8 to 10 mm of mercury.

The elbow pouch 15 here is knitted so as to be oversized or loose relative to the lower arm and upper arm portions. This is done by programming the machine to loosen and open up each knitted loop of the stitching.

The stitch loops of the oversized elbow pouch are knitted looser than the stitch loops of the upper arm and lower arm portions so as to have some one-third or more elongation than these other portions. As such, the elbow pouch has a compression force that is less than the compression force of the upper arm portion. This is especially beneficial where a wound dressing has been applied to a patient's elbow area. This construction also insures that minimal tension is placed on the yarns of the elbow pouch while the compression wrap is being donned. The compression force of the elbow pouch may be less than that of the upper arm portion without causing blood pooling. The oversized elbow pouch forms a less restrictive pocket for the elbow to fit. Without this aspect, the fabric is stretched vertically around the elbow, which could compromise the horizontal compression at the elbow.

The elbow crest 16 is knitted in a manner that substantially prevents it from wrinkling when donned as would occur if it were of the same stitch format as that of the elbow pouch, upper arm portion or lower arm portion. This is achieved by programming the knitting machine to gather the excess stitches here into a multi-ribbed format, wherein the ribs extend longitudinally up the arm between the lower arm portion and upper arm portion. Once donned the gathered ribs become ungathered and smooth without wrinkles. Otherwise, were wrinkles to remain here the skin beneath this arch would become subject to abrasion.

Figure 5A:
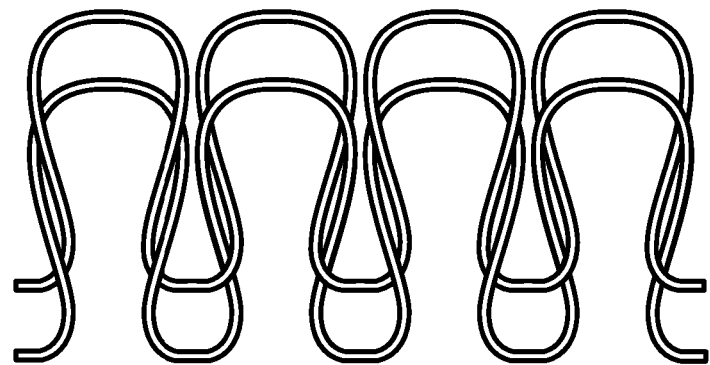
FIG. 5A-5C illustrated 1×1, 2×2 and 3×1 knit rib formats, respectively.
Figure 5B:
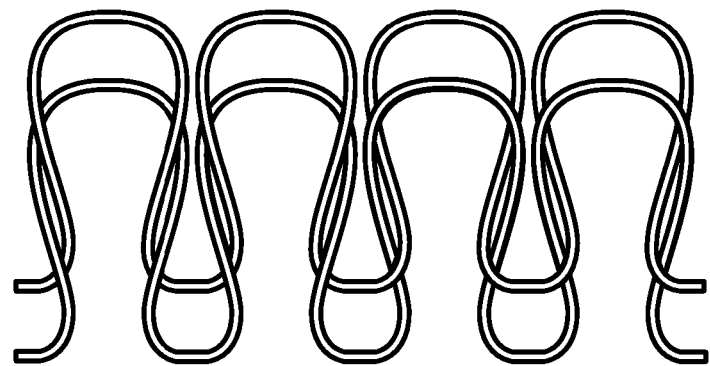
Figure 5C:
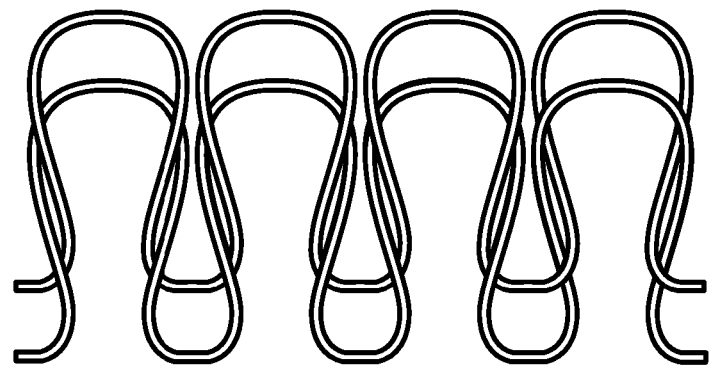

The elbow crest is preferably knitted in a 1×1, a 2×2 or a 3×1 rib format, depending on the thermo-plastic properties, modulus and size of the yarns. These formats are illustrated in FIGS. 5A-5C. In FIG. 5A it is seen that alternating wales are looped to the front and then to the back. As viewed here from left to right, the upper loop is over the top of the lower. The next loop is under, the next over, the next under, and so forth. This is a 1×1 format. In FIG. 5B every two adjacent wales are looped over and the next two under, again as viewed from left to right. This is a 2×2 format. FIG. 5C shows a 3×1 rib format or structure where three wales are looped over and then one wale is looped under, and so forth. Preferably the elbow crest is knitted directly to the elbow pouch although this is not essential.

The preferred compression wrap yarns here are stretch nylon or stretch polyester and spandex, spandex being an elastic fiber sold under the trade name LYCRA and available from E. I. DuPont de Nemours and Company, Wilmington, Del., U.S.A. Stretch nylon and spandex are synthetic fibers that are resilient. The degree of stretch and recovery of these fibers can be thermally altered to a desired modulus.

Figure 3:
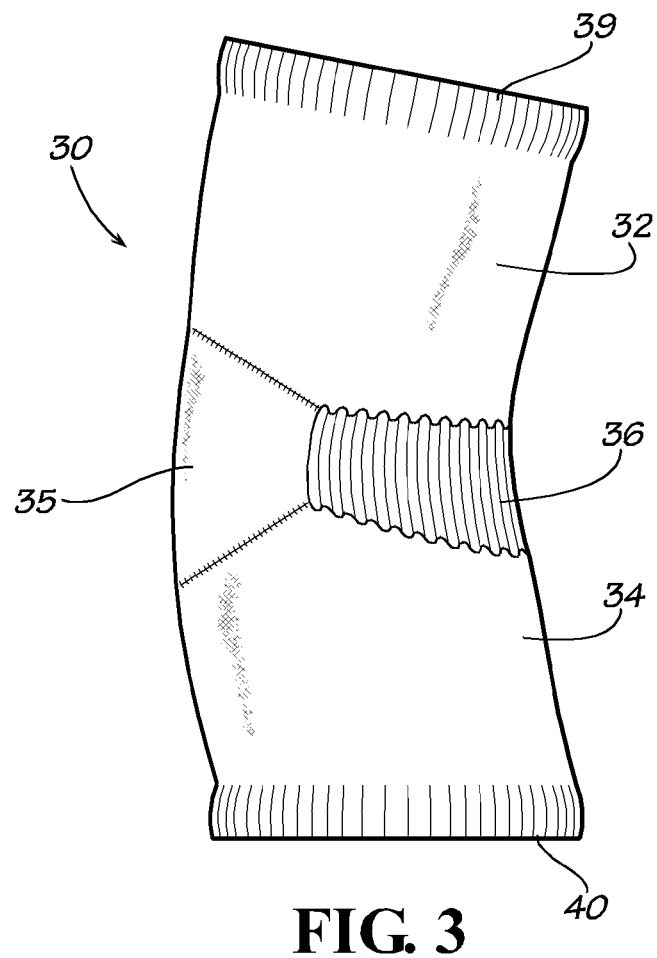
FIG. 3 is a side view of another preferred form of the compression joint wrap shown in a worn state.
Figure 4:
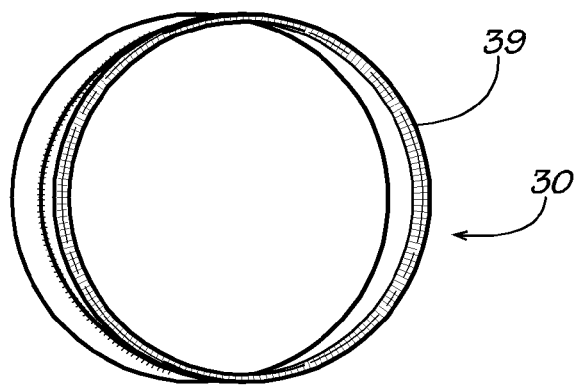
FIG. 4 is a top view of the joint compression wrap of FIG. 3.

With reference next to FIGS. 3 and 4, there is shown a seamless joint compression wrap in the form of a knee compression wrap 30. The knee compression wrap 30 is essentially the same as the previously described elbow compression wrap except that it is configured to fit over the knee area of a person. The compression wrap 30 is seen to have a upper limb or leg portion 32 joined to a lower limb or leg portion 34 by a front or anterior knee pouch 35 and a back, posterior or dorsal joint or knee crest 36. The top of the upper leg portion 32 is formed with an upper cuff 39. The bottom of the lower leg portion 34 is formed with a lower cuff 40. The compression wrap may, of course, be produced in any number of overall sizes to fit patients of different sizes The compression wrap is efficiently produced in an integrated knit stitch format with a knitting machine that has needle by needle selection capability in order to produce a compression wrap without seams. The knit format is essentially the same as previously described in reference to the elbow compression wrap except that the compression of both the upper leg portion and lower leg portion are static rather than the graduated compression previously described in reference to the upper arm portion. It should be understood, however, that the knee compression wrap may also be made with a graduated compression upper leg portion.

The term wrinkles or wrinkling is intended to mean unintended bends or crimps in yarn, mis-shaped stitches, or excess material that adversely affects the presentation, hand, or performance of a fabric or the end product.

It thus is seen that a joint compression wrap may now be manufactured in an integrated knit stitch format that my be donned with facility over the joint and which provides improved graduated pressure all without wrinkling of the compression wrap over the back knee crest. Although the compression wrap has been illustrated and described in its preferred form, it should be understood that many modifications, additions and deletions may be made to that specific form without departure from the spirit and scope of the invention as set forth in the following claims.

The invention claimed is:

1. A joint compression wrap comprising a lower limb portion configured to fit about a human limb directly below a limb joint and having a knit format and yarn to produce a first compression force, a joint crest configured to fit over a human limb joint and coupled to said lower limb portion having a knit format and yarn to produce a second compression force equal to or less than said first compression force, and an upper limb portion coupled to said joint crest opposite said lower limb portion having a knit format and yarn to produce a third compression force of a graduated compression type wherein the compression force decreases along the upper limb portion from a first end adjacent said joint crest to a second end distal said joint crest.

2. The joint compression wrap of claim 1 wherein said lower limb portion second compression force is generally constant along the entire length of said lower limb portion.

3. The joint compression wrap of claim 1 further comprising a joint pouch portion coupled to and between said lower limb portion and said upper limb portion and oppositely disposed from said joint crest, said joint pouch portion having a fourth compression force less than said upper limb portion third compression force.

4. The joint compression wrap of claim 1 wherein said joint crest knit format is in a pattern of ribs that extend side by side in a longitudinal direction between said upper limb portion and said low limb portion.

5. The joint compression wrap of claim 1 wherein said lower limb portion, said joint crest and said upper limb portion are constructed of an integrated knit stitch format which produces no seams between adjacent portions.

6. The joint concession wrap of claim 1 wherein said upper limb portion is configured to fit about the leg of a human directly above the knee, wherein said lower limb portion is configured to fit about the leg of a human directly below the knee, and the joint crest is configured to fit upon the back of the knee.

7. The joint compression wrap of claim 1 wherein said upper limb portion is configured to fit about the arm of a human directly above the elbow, wherein said lower limb portion is configured to fit about the arm of a human directly below the elbow, and the joint crest is configured to fit upon the front of the elbow.

8. A joint compression wrap having tubular knitted yarn lower limb portion and upper limb portion joined by a knitted yarn joint crest portion, wherein said lower limb portion is knitted with a constant compression format, wherein said upper limb portion is knitted with a graduated knit format that decreases the compression force of the compression wrap upper limb portion from a first end adjacent said joint crest portion to a second end distal said joint crest portion.

9. The joint compression wrap of claim 8 wherein said lower limb portion constant compression format has a first compression force and said upper limb portion graduated knit format has a second compression force less than said first compression force.

10. The joint compression wrap of claim 8 wherein said joint crest portion has a third compression force, and wherein said joint crest portion third compression force is greater than said upper limb portion second compression force.

11. The joint compression wrap of claim 10 further comprising a joint pouch portion coupled to and between said lower limb portion and said upper limb portion and oppositely disposed from said point crest portion, said joint pouch portion having a fourth compression force less than said upper limb portion second compression force.

12. The joint compression wrap of claim 8 wherein said joint crest portion knit format is in a pattern of ribs that extend side by side in a longitudinal direction between the upper limb and lower limb portions.

13. The joint compression wrap of claim 8 wherein said lower limb portion, said joint crest portion and said upper limb portion are constructed of an integrated knit stitch format which produces no seams between adjacent portions.

14. The joint compression wrap of claim 8 wherein said upper limb portion is configured to fit about the leg of a human directly above the knee, wherein said lower limb portion is configured to fit about the leg of a human directly below the knee, and the joint crest portion is configured to fit upon the back of the knee.

15. The joint compression wrap of claim 8 wherein said upper limb portion is configured to fit about the arm of a human directly above the elbow, wherein said lower limb portion is configured to fit about the arm of a human directly below the elbow, and the joint crest portion is configured to fit upon the front of the elbow.

* * * * *